(12) United States Patent
Lezdey et al.

(10) Patent No.: US 6,262,020 B1
(45) Date of Patent: Jul. 17, 2001

(54) TOPICAL WOUND THERAPEUTIC COMPOSITIONS

(75) Inventors: John Lezdey; Darren B. Lezdey, both of Indian Rocks Beach, FL (US)

(73) Assignee: Alphamed Pharmaceuticals Corp., Clearwater, FL (US)

( * ) Notice: Subject to any disclaimer, the term of this patent is extended or adjusted under 35 U.S.C. 154(b) by 0 days.

(21) Appl. No.: 09/503,833

(22) Filed: Feb. 15, 2000

(51) Int. Cl.⁷ .................. A61K 38/16; A61K 38/00; A61K 31/74; A61K 9/127
(52) U.S. Cl. .................. 514/8; 514/2; 514/21; 424/78.06; 424/450
(58) Field of Search .................. 514/8, 944; 424/450

(56) References Cited

U.S. PATENT DOCUMENTS 5,604,200 * 2/1997 Taylor-McCord .................. 514/8
6,056,970 * 5/2000 Greenawalt et al. .................. 424/426

* cited by examiner

*Primary Examiner*—Shep K. Rose
*Assistant Examiner*—Donna Jagoe
(74) *Attorney, Agent, or Firm*—John Lezdey & Assoc

(57) ABSTRACT

There is provided a composition for healing burns and wounds in mammals which contains the combination of hyaluronic acid and a serine protease inhibitor.

Advantageously, elements found in amniotic fluid are also included.

8 Claims, No Drawings

TOPICAL WOUND THERAPEUTIC COMPOSITIONS

BACKGROUND OF INVENTION

1. Field of the Invention

This invention relates the treatment of burns, open sores, incisions and wounds in mammals. In particular it relates to topical wound therapeutic formulations containing a hyaluronic acid (hyaluronan) and a serine protease inhibitor, preferable in combination with elements found in amniotic fluid.

2. Description of the Prior Art

Adult wound repair is characterized by fibrosis, scarring, and sometimes by contracture. The results of this deforming process affect every form of surgery and can have devastating consequences. In contrast fetal wound healing proceeds without such fibrosis or scar formation, Michael T. Longaker, M.D., Ernie S. Chiu, B.S., N. Scott Adzick, M.D., Michael Stern, D.D.S., Michael R. Harrison, M.D., and Robert Stern, M.D., *Studies in Fetal Wound Healing, V. A Prolonged Presence of Hyaluronic Acid Characterizes Fetal Wound Fluid*, Ann Surg, April 1991, pp. 292–296.

It is known that hyaluronic acid bonds with fibronectin and together they have a powerful effect on the body's cellular matrix. It is also known that urea, produced by the fetus has an effect on cell migration. Elements such as glucose, protein, sodium, potassium, calcium, magnesium, phosphate and chloride that form the amniotic fluid, work together with an inseparable bond and synergy.

Fibronectin is important in wound healing. However, the presence of certain proteases in excess binds with the fibronectin and prevents its activity in healing.

Several prior art patents disclose therapeutic formulations including hyaluronic acid. Lindblad, "Hyaluronic Acid Preparation used for Treating Inflammations of Skeletal Joints"; U.S. Pat. No. 4,801,619 disclosed the use of hyaluronic for intra-articular administration for the treatment of steroid arthropathy and progressive cartilage degeneration caused by protoglycan degradation. Langerman, "Spare Parts for Use in Ophthalmic Surgical Prodecures: U.S. Pat. No. 4,888,016 disclosed the use of hyaluronic acid in ophthalmic surgery as an artificial "spare part" for surgical implantation in the eye during an extracapsular cataract extraction. Alvarez, "Three Step Wound Treatment Method and Dressing Therefor"; U.S. Pat. No. 4, 813,942, which is herein incorporated by reference, disclosed the use of hyaluronic acid in the third step of a three step treatment. The invention calls for hyaluronic acid to be in a hydrocolloid dressing which will provide controlled delivery over a period of 24 to 96 hours to promote thickening of the epidermal cells, thus strengthening the wound. Balazs et al, "Cross-Linked Gels of Hyaluronic Acid and Products Containing Such Gels"; U.S. Pat. Nos. 4,582,865, 4,636,524 and 4,636,865 disclosed the use of cross linked gels of hyaluronic acid as a drug delivery system.

None of these prior art references claim to use hyaluronic acid and a serine protease inhibitor in the treatment of burns, open sores, incisions, and wounds and there is no combination with calcium, phosphate, uric acid, urea, sodium, potassium, chloride, and magnesium to simulate amniotic fluid.

U.S. Pat. Nos. 5,190,917 and 5,290,762, which are herein incorporated by reference disclose the roles of serine protease inhibitors in treatment of inflammation.

U.S. Pat. No. 4,970,298 which is herein incorporated by reference discloses a biodegradable matrix which comprises collagen, hyaluronic acid and fibronectin which enhance healing of wounds. Collagen, which is oversecreted by the body in response to an injury or wound, is known to be responsible for scar formation. Georgalas et al., "Skin Treatment Composition and Method for Treating Burned Skin," U.S. Pat. No. 4,839,019, discloses a composition which counteracts moisture loss and promotes healing of burned or sunburned skin comprised of polyglycerylmethacrylate, glycerine, allantoin, panthenol, amino acid complex, and fibronectin.

BRIEF SUMMARY OF THE INVENTION

The invention relates to formulations containing hyaluronic acid and a serine protease inhibitor selected from the group consisting of alpha 1-antitrypsin (AAT), secretory leucocyte protease inhibitor (SLPI) and cromolyn. The mixture can be further combined with calcium, phosphate, uric acid, urea, sodium, potassium, chloride and magnesium, all elements found in amniotic fluid, to provide a unique synergy that is effective in the treatment of burns, open sores, incisions and wounds in mammals.

The invention is used for wound therapeutic formulations useful for topical application, useful for treating burns, traumatic damage caused by irradiation of the skin, the deleterious effects of open sores, incisions and wounds on skin and further provides a mixture which simulates the fetal in utero wound healing matrix in a safe and effective amount of a topical carrier.

Hyaluronic acid and the serine protease inhibitor alone in a pharmaceutical base are sufficient for treating minor injuries. The additional elements comprise a mixture of constituents selected from the group of calcium, phosphate, uric acid, urea, sodium, potassium, chloride and magnesium which are found in amniotic fluid.

A preferred topical composition comprises by weight of the mixture: 0.01% to 1.50% calcium; 0.01% to 0.10% phosphate; 0.01% to 2.00% uric acid, 0.01% to 2.00% urea; 0.02% to 1.50% sodium; 0.01% to 0.10% potassium; 0.01% to 0.70% chloride; 0.001% to 0.01% magnesium; 0.01% to 2.50% hyaluronic acid; and 0.01% to 5.00% of a protease inhibitor.

In the best mode the hyaluronic acid comprises by weight 0.10% to 2.50% of the mixture either with the serine protease inhibitors alone or with the additional elements.

DETAILED DESCRIPTION OF THE PREFERRED EMBODIMENTS

The invention is a means for delivery of hyaluronic acid and a serine protease inhibitor in a topical preparation for the treatment of burns, open sores, incisions and wounds for optimum healing.

In accordance with the invention, there is provided herein formulations useful for topical application comprising hyaluronic acid and a serine protease inhibitor alone or in combination with calcium, phosphate, uric acid, urea, sodium, potassium, chloride, and magnesium, all elements healing matrix and a safe and effective amount of a topical carrier, in combinations described below.

Tissue repair in the mammalian fetus is fundamentally different than normal adult healing. In adult humans, injured tissue is repaired by collagen deposition, collagen remodeling and eventual scar formation, whereas fetal wound healing appears to be more of a regenerative process with minimal or no scar formation. The adult wound heals by the replacement of normal dermis with a scar that consists of excessive and abnormally organized collagen. In marked contrast, the fetal wound contains a persistent abundance of hyaluronic acid while collagen deposition is rapid and nonexcessive, Bruce A Mast, M.D., Robert F. Diegelmann, Ph.D., *Healing in the Mammalian Fetus*, Surg. Gyn. And Ob., Vol. 174, pp. 441–451, May 92.

What is known is that hyaluronic acid has a definite role in harnessing and manipulating the natural reparative capacity of tissue fibroblasts and the hyaluronic acid protein complexes play a significant role in vivo organization or scar tissue, D. A. R. Burd, R. M. Greco, S. Regaurer, M. T. Longaker, J. W. Siebert and H. G. Garg, *Hyaluronan and Wound Healing: a New Perspective*, Journal of Plastic Surgery, 1991, pp. 579–584.

Hyaluronic acid has played a very limited role in the care and treatment of burns, open sores, incisions and wounds because there has not been an effective delivery system that could deliver hyaluronic acid, which is found in abundance in amniotic fluid, to the wound site in a manner that replicated the moist environment and the other healing benefits discovered in amniotic fluid.

It is understood that the term hyaluronic acid includes its derivatives and broadly refers to naturally occurring, microbial and synthetic derivatives of acidic polysaccharides of various molecular weights constituted by residues of glucuronic acid and N-acetyl-D-glucosamine.

Serine protease inhibitors, because of their control of elastase, permit proper laying down of tissue and can prevent keloid scars. The serine protease inhibitor is used in an amount of about 0.5 to 5% by weight of the composition.

The wound healing process is significantly different in adults as compared to the healing that takes place in amniotic fluid. Sharply increased levels of hyaluronic acid characterize adult wound healing during the first three days. By the seventh day, hyaluronic acid is not detectable. In adults, wound healing is believed to be accomplished by high levels of alpha 1-antitrypsin and it is further believed that it is the elastase that is responsible for scarring and needs to be controlled together with cathepsin G.

Fetal wound healing is characterized by sharply increased levels of hyaluronic acid during the first three days, but, unlike adult wound healing the level of hyaluronic acid remains elevated for 21 days. These findings are the result of research conducted by Michael T. Longaker, M.D., Ernie R. Harrison, M.D., and Robert Stern, M.D. and reported in an article titled *Studies in Fetal Wound Healing: V. A. Prolonged Presence of Hyaluronic Acid Characterizes Fetal Wound Fluid*, in Ann. Surg., April 1991, pp. 292–296. The graph of their findings as published is shown in FIG. 1.

The healing process of the fetus is controlled by high levels of hyaluronic acid and alpha 1-antitrypsin. In adult healing process there is an overproduction of elastase which leads to the formation of scar tissue. The topical addition of hyaluronic acid and an elastase binding protease inhibitor in the wound bed will alter the adult healing process and facilitate accelerated healing and reduce the formation of scar tissue. The presence of both the hyaluronic acid and alpha 1-antitrypsin protects fibronectin from being degraded by elastase and other proteases.

Cell growth stimulating compound, may be incorporated into the composition. According to the present invention, the human growth hormone is utilized in an effective amount of at least about 0.05 ng/ml. Most preferably, the cell growth stimulating compound includes a mixture of human growth hormone, insulin (containing transferrin or transferrin-free) and/or triiodothyronine or thyroxin, each compound in an amount ranging from at least about 0.05 ng/ml, preferably at least about 0.5 ng/ml, and more preferably at least 1 ng/ml or more. In the case of insulin, the effective amount of insulin generally ranges from about 5 ng/ml to about 100 ug/ml and more preferably about 50 ng/ml to about 2 ug/ml within this range.

In addition to effective amount of cellular growth stimulating hormone and cellular nutrient media, formulations according to the present invention may also contain hydrocortisone, which in certain instances may have a beneficial overall effect in enhancing wound healing.

Hydrocortisone is found to improve the cloning efficiency of fibroblasts, enhancing the maintenance of epidermal keratinocytes. The preferred amount to be incorporated is generally within the range of about 0.2 umol to about 50 umol. The formulations according to the present invention may also include an effective amount of an antimicrobial agent, for example, antibiotics and antifungal agents, such as griseofulvin and nystatin and antiviral agents and the like. The antimicrobial agent may be added for its ability to treat an infection, or alternatively, for its prophylactic effect in avoiding an infection.

There are many different carriers which can effect quick delivery to the skin. Such delivery system is desirable especially in dogs who have the tendency to lick their wounds. Therefore, a liposome which causes a rapid infusion into the skin is desirable. One such delivery system is found in "Novasome" a trademark for a carrier of Eavsco Corp. of New Jersey.

Otherwise, an occlusive bandage type of carrier such as vasoline or aquaphor can be used.

EXAMPLE 1

A Therapeutic Skin Lotion

A therapeutic aqueous skin lotion is prepared by combining the following components utilizing conventional mixing techniques.

| INGREDIENT | PERCENTAGE BY WEIGHT |
| --- | --- |
| Aloe Vera Gel | 2.50% |
| Walnut Oil | 2.00% |
| Tocopherol Acetate (Vitamin) | 2.00% |
| Glycerin | 2.00% |
| Stearic Acid | 2.00% |
| 1-Hexadecanol | 2.00% |
| Polysorbate 60 | 2.00% |
| Apricot Kernal Oil | 2.00% |
| Jojoba Oil | 2.00% |
| Glyceryl Sterate | 2.00% |
| PEG-100 Stearate | 1.00% |
| Alpha 1-antitrypsin | 1.00% |
| Dimethicone | 1.00% |
| PVP | 1.00% |
| Hyaluronic Acid | 0.50% |
| Sodium | 0.50% |
| Allantoin | 0.50% |
| Triethanolamine | 0.50% |
| Carboner-940 | 0.20% |
| Chloride | 0.20% |
| Potassium | 0.05% |
| Urea | 0.06% |
| Calcium | 0.05% |
| Phosphate | 0.03% |
| Magnesium | 0.01% |

EXAMPLE 2

A Therapeutic Skin Gel

A therapeutic skin gel is prepared by combining the following components utilizing conventional mixing techniques.

| INGREDIENT | PERCENTAGE BY WEIGHT |
| --- | --- |
| Water | 90.90% |
| Aloe vera extract | 2.00% |
| Glycerin | 2.00% |
| PVP | 1.00% |
| Triethanonmine | 1.00% |
| Sodium | 0.70% |
| Hyaluronic Acid | 0.50% |
| Alpha 1-antitrypsin | 0.50% |
| Allantoin | 0.50% |
| Carbomer-940 | 0.50% |
| Chloride | 0.50% |
| Potassium | 0.05% |
| Urea | 0.06% |
| Calcium | 0.05% |
| Phosphate | 0.03% |
| Magnesium | 0.01% |

EXAMPLE 3

Into Novasome of Eavsco Corp. is admixed 1.0% by weight of alpha 1-antitrypsin and 1.0% of hyaluronic acid for use in treating hot spots on dogs.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims. The following claims are, therefore, to be read to include not only the combination of elements which are literally set forth, but all equivalent elements for performing substantially the same function in substantially the same way to obtain substantially the same result. The claims are thus to be understood to include what is specifically illustrated and described above, what is conceptionally equivalent, and also what essentially incorporates the germ of the invention.

What is claimed is:

1. A substantially collagen-free fluid composition for the treatment of chronic burns, open sores, incisions and wounds in mammals composition comprising:

Hyaluronic acid;

Alpha 1-antitrypsin; and a topical solution comprising a mixture of four or more constituents selected from the group consisting of calcium, phosphate, uric acid, urea, sodium, potassium, chloride and magnesium.

2. The composition of claim 1 wherein said topical solution comprises a pharmaceutically acceptable fluid carrier.

3. The fluid composition of claim 1 wherein said medical hyaluronic acid comprises by weight 0.01% to 2.00% of said composition, wherein said alpha 1-antitrypsin comprises by weight 0.01% to 5.00% of said composition, and wherein said topical solution comprises by weight of said mixture:

0.01% to 1.50% calcium;

0.01% to 0.10% phosphate;

0.01% to 2.00% uric acid;

0.01% to 2.00% urea;

0.02% to 1.50% sodium;

0.01% to 0.10% potassium;

0.01% to 0.70% chloride; and 0.001% to 0.01% magnesium.

4. A composition for topically treating burns, open sores, incisions and wounds in mammals which comprise a therapeutically effective amount of alpha 1-antitrypsin in combination with a synergistically effective amount of hyaluronic acid and a solution comprising a mixture of at least four constituents selected from the group consisting of calcium, phosphate, uric acid, urea, sodium, potassium, chloride and magnesium to increase skin penetration in a suitable fluid carrier, so as to treat burns, open sores, incisions and wounds.

5. The composition of claim 4 wherein said carrier comprises a liposome.

6. The composition of claim 4 including a steroid.

7. The composition of claim 4 including a human growth hormone.

8. The composition of claim 7 including insulin.

\* \* \* \* \*